(12) United States Patent
Sup, IV et al.

(10) Patent No.: US 10,226,363 B2
(45) Date of Patent: Mar. 12, 2019

(54) PROSTHETIC SOCKET FITMENT SYSTEM

(71) Applicants: Frank Charles Sup, IV, Amherst, MA (US); Andrew Kennedy LaPre, Amherst, MA (US); Michael White, Amherst, MA (US)

(72) Inventors: Frank Charles Sup, IV, Amherst, MA (US); Andrew Kennedy LaPre, Amherst, MA (US); Michael White, Amherst, MA (US)

(73) Assignees: University of Massachusetts, Boston, MA (US); FTL Labs Corporation, Amherst, MA (US)

( * ) Notice: Subject to any disclaimer, the term of this patent is extended or adjusted under 35 U.S.C. 154(b) by 28 days.

(21) Appl. No.: 15/185,632

(22) Filed: Jun. 17, 2016

(65) Prior Publication Data

US 2016/0367386 A1 Dec. 22, 2016

Related U.S. Application Data

(60) Provisional application No. 62/181,603, filed on Jun. 18, 2015.

(51) Int. Cl.
*A61F 2/76* (2006.01)
*A61F 2/80* (2006.01)
*A61F 2/78* (2006.01)

(52) U.S. Cl.
CPC .................. *A61F 2/76* (2013.01); *A61F 2/80* (2013.01); *A61F 2/7812* (2013.01)

(58) Field of Classification Search
CPC .......................................................... A61F 2/76
See application file for complete search history.

(56) References Cited

U.S. PATENT DOCUMENTS

| 3,805,227 | A | * | 4/1974 | Lester | G08B 3/1083 |
| | | | | | 16/DIG. 13 |
| 4,923,476 | A | | 5/1990 | Cooper et al. | |
| 5,056,367 | A | * | 10/1991 | Marshall | G01B 17/00 |
| | | | | | 367/127 |
| 5,127,420 | A | | 7/1992 | Horvath | |
| 6,383,139 | B1 | * | 5/2002 | Hwang | A61B 8/00 |
| | | | | | 600/441 |

(Continued)

OTHER PUBLICATIONS

Amstutz, Christoph, et al., "A-Mode Ultrasound-Based Registration in Computer-Aided Surgery of the Skull", Arch Otolaryngol Head Neck Surgery, vol. 129, [Online]. Retrieved from the Internet: <URL: http://archotol.jamanetwork.com, (Dec. 2003), 1310-1316.

(Continued)

*Primary Examiner* — Jacqueline Woznicki
(74) *Attorney, Agent, or Firm* — Schwegman Lundber & Woessner, P.A.

(57) ABSTRACT

A prosthetic socket fitment system for fitting a prosthesis to a patient can include at least one transceiver assembly in contact with an external frame coupled to a patient, and a processing module in electrical communication with the at least one transceiver assembly. The at least one transceiver assembly can be aligned to the bone of the patient and configured to generate a signal directed to the bone of the patient and receive a reflected signal from the bone of the patient.

20 Claims, 11 Drawing Sheets

(56) References Cited

U.S. PATENT DOCUMENTS

| | | | | |
|---|---|---|---|---|
| 8,656,918 | B1* | 2/2014 | Alley | A61F 2/76 128/845 |
| 8,784,502 | B2 | 7/2014 | Macomber et al. | |
| 2006/0179935 | A1* | 8/2006 | Warila | A61F 2/76 73/172 |
| 2006/0212128 | A1* | 9/2006 | Nachbar | A61F 2/60 623/24 |
| 2008/0243266 | A1* | 10/2008 | Haynes | A61F 2/68 623/34 |
| 2010/0161077 | A1* | 6/2010 | Boone | A61F 2/60 623/38 |
| 2014/0121783 | A1* | 5/2014 | Alley | A61F 2/76 623/33 |
| 2015/0168943 | A1* | 6/2015 | Hurley | A61F 2/5046 700/98 |
| 2016/0331563 | A1* | 11/2016 | Kane | A61F 2/76 |

OTHER PUBLICATIONS

Boone, David, et al., "In?uence of malalignment on socket reaction moments during gait in amputees with transtibial prostheses", Gait & Posture 37, (2013), 620-626.

Convery, P., et al., "Ultrasound study of the motion of the residual femur within a trans-femoral socket during gait", Prosthetics and Orthotics International, (2000), 226-232.

Heger, Stefan, et al., "A-Mode Ultrasound-based intra-femoral Bone Cement Detection and 3D Reconstruction in RTHR", Computer Aided Surgery. 12(3), [Online]. Retrieved from the Internet: <URL: http://www.tandfonline.com/action/journal/Information?journalCode=icsu20>, (May 2007), 168-175.

Heger, Stefan, et al., "User-Interactive Registration of a Bone with A-Mode Ultrasound", IEEE Engineering in Medicine and Biology Magazine, (Mar./Apr. 2005), 85-95.

Mozes, Alon, et al., "Three-Dimensional A-Mode Ultrasound Calibration and Registration for Robotic Orthopaedic Knee Surgery", Int J Med Robotics Comput Assist Surg, 6, (2010), 91-101.

Portnoy, S, et al., "Internal Mechanical Conditions in the Soft Tissues of a Residual Limb of a Trans-tibial Amputee", Journal of Biomechanics 41, (2008), 1897-1909.

Schiff, Adam, et al., "Quantification of Shear Stresses Within a Transtibial Prosthetic Socket", Foot & Ankle International, (2014), 1-4.

Giannetti, Romano, et al., "Feasibility Study of In Vivo Bone Depth Measurement using High Frequency Ultrasound", IEEE, (2015), 5 pgs.

* cited by examiner

PROSTHETIC SOCKET FITMENT SYSTEM

CLAIM OF PRIORITY

This patent application claims the benefit of priority of U.S. Provisional Patent Application Ser. No. 62/181,603, entitled "Prosthetic Socket Fitment System," filed on Jun. 18, 2015, which is hereby incorporated by reference herein in its entirety.

BACKGROUND

The process of fitting sockets to replace a human limb is a labor-intensive process that can result in sockets that are uncomfortable, unstable, or impede the full range of motion of the prosthetic limb.

A variety of systems exist for fitting patients with limb prostheses. For example, U.S. Pat. No. 8,784,502 mentions an alignment system with a transducer that can measure socket reactions in the anterior/posterior plane and the right/left planes, while canceling or reducing the transverse forces in measuring socket reactions.

U.S. Pat. No. 5,127,420 mentions a computerized prosthesis alignment system and includes a transducer that can measure socket reactions in the anterior/posterior plane and the right/left planes.

U.S. Pat. No. 4,923,476 mentions an alignment device comprising first and second end plates fastenable to respective upper and lower parts of the limb in a predetermined angular and axial position and a flexible sleeve fastened between the end plates that can form an internal cavity for containing a body of settable fluid.

OVERVIEW

A prosthetic socket fitment system for fitting a prosthesis to a patient can include at least one transceiver assembly in contact with an external frame coupled to a patient, and a processing module in electrical communication with the at least one transceiver assembly. The at least one transceiver assembly can be aligned to the bone of the patient and configured to generate a signal directed to the bone of the patient and receive a reflected signal from the bone of the patient.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
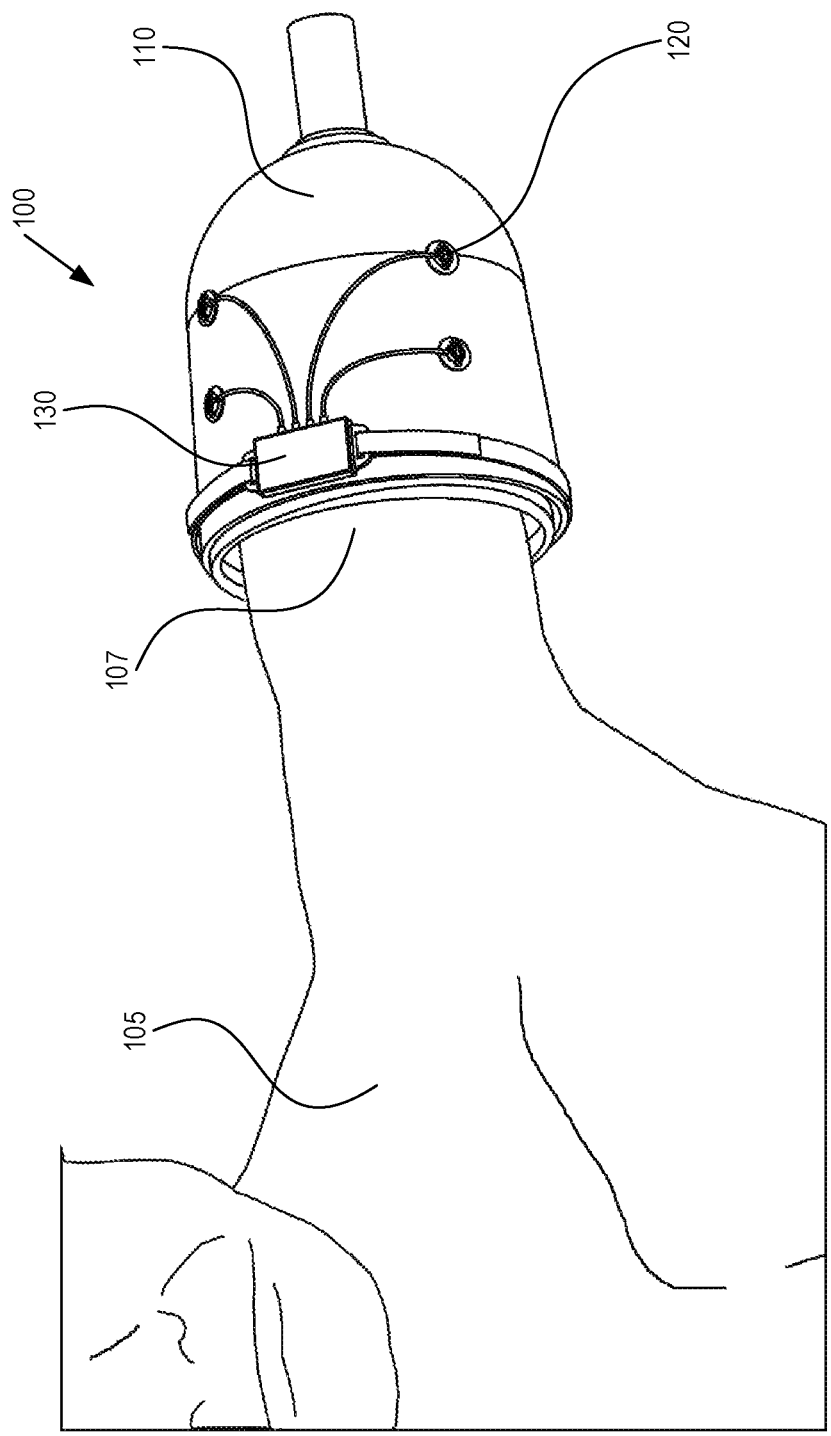
FIG. 1 shows an example of a prosthetic socket fitment system.

FIG. 1 shows an example of a prosthetic socket fitment system 100 that can be used in fitting an artificial limb to a patient 105. In an example, an artificial limb can include at least one of a prosthesis, such as a medical prosthesis to replace a missing limb, and an exoskeleton device to enhance human movement and capability. In an example, the prosthetic socket fitment system 100 can include an external frame 110, a transceiver assembly 120, and a processing module 130. In an example, the external frame 110 can be fitted to the residual limb 107 of a patient 105, such as to carry a prosthesis. An external frame 110 can include a device used in the fitting of an artificial limb to a patient 105, such as a device located between the patient 105 and the artificial limb including as least one of a socket shell and an exoskeleton cuff, and a tool that can be used to fabricate a device for location between the patient 105 and the artificial limb. In an example, the prosthetic socket fitment system 100 can be used in conjunction with the methods, systems, and tools described in the U.S. Pat. No. 8,656,918 issued Feb. 25, 2014 to Alley, et al. In an example, the prosthetic socket fitment system 100 can be used to improve the fitment of the external frame 110 to the residual limb 107, such as to improve the comfort of the external frame 110 that is fitted to the patient 105. In an example, an ultrasonic transceiver can be used to generate ultrasound, such as to map the relative distance from the external frame 110 to the bone of a residual limb 107.

Figure 2A:
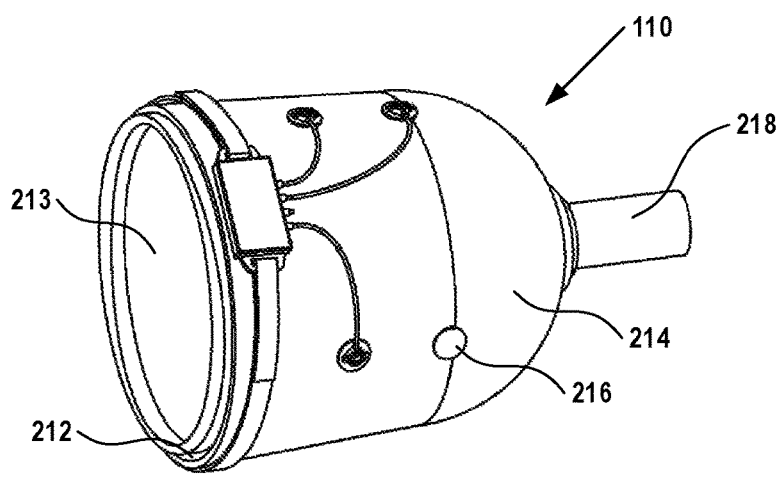
FIG. 2A shows an isometric view of an example socket shell.

FIG. 2A shows an isometric view of an example external frame 110. In an example, the external frame 110 can include an inner surface 212, and an outer surface 214, generally parallel to the inner surface 212. In an example, the external frame 110 can include an interface surface 213, such as to be generally parallel to the inner surface 212. In an example, the interface surface 213 can include contact with at least a portion of the residual limb 107.

Figure 2B:
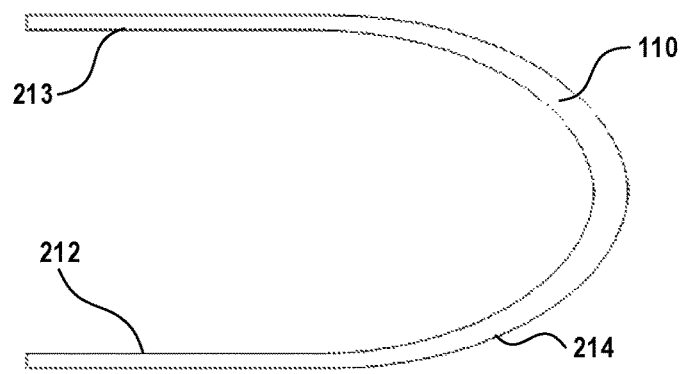
FIG. 2B shows a cross sectional view of an example socket shell.

FIG. 2B shows a cross sectional view of an example external frame 110. In an example, the inner surface 212 and the interface surface 213 can coincide, such as to be the same surface.

Figure 2C:
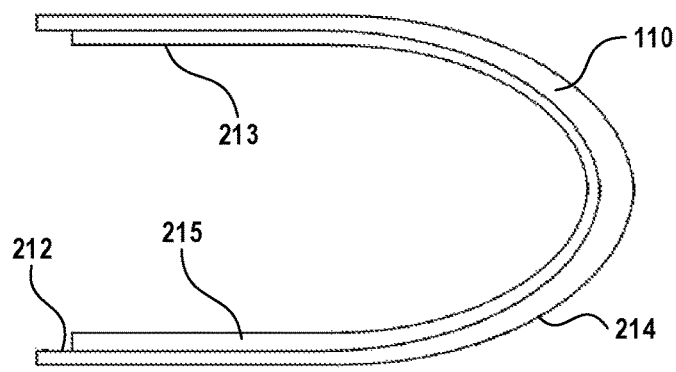
FIG. 2C shows a cross sectional view of an example socket shell that can include a liner.

FIG. 2C shows a cross sectional view of an example external frame 110 that can include a liner 215. In an example, the liner 215 can contact the inner surface 212 of the external frame 110, such that the surface of the liner 215 opposite the inner surface 212 can form the interface surface 213. For example, the liner 215 can be located between the residual limb 107 and the external frame 110, such that a surface of the liner 215 can be in contact with the inner surface 112 of the external frame 110 and the opposite surface of the liner 215 can be in contact with the residual limb 107, such as to form the interface surface 213. The liner 215 can include any suitable biocompatible material. In an example, the liner 215 can include a flexible material, such as a fabric, a thermoplastic, a viscoelastic material such as a gel pad, or a combination of the aforementioned materials.

The surface area of the interface surface 213 can be in contact with a portion of the surface area of the residual limb 107. For example, the percentage of contact area between the surface area of the interface surface 213 and the surface area of the residual limb 107 can include any value from approximately 0 percent to approximately 100 percent of the interface surface 213, such as 10%, 30%, 50%, 70%, 90%, or other percentage contact area.

The external frame 110 can be constructed from natural materials, such as wood, man-made materials, such as plastics including thermoplastics, nylon, and acrylonitrile butadiene styrene (ABS), composites, such as carbon fiber and Kevlar, or other types of materials. In an example, the material selected to construct the external frame 110 can include characteristics beneficial to the function of the external frame 110, such as strength, rigidity, moldability, and density. The material used to construct the external frame 110 can include materials with high transmissibility to mechanical energy, such as sonic or ultrasonic energy. For example, sonic energy can include energy transmitted in frequency ranges from approximately 0 hertz to approximately 20,000 hertz and ultrasonic energy can include energy transmitted in frequency ranges greater than approximately 20,000 hertz. Transmissibility can relate to the ability of a material to transmit mechanical energy from a first location to a second location.

The external frame 110 can include a transceiver cavity 216, such as one or more transceiver cavities 216. In an example, the transceiver cavity 216 can extend from the outer surface 214 to a point in the external frame 110 between the inner surface 212 and the outer surface 214. In an example, the transceiver cavity 216 can extend from the outer surface 214 completely through the external frame 110 to the inner surface 212, such as to form a hole between the outer surface 214 and the inner surface 212 of the external frame 110.

The transceiver cavity 216 can be configured to receive a removable component, such as a transceiver assembly, at a fixed position with respect to the external frame 110. The transceiver cavity 216 can be configured to locate the removable component in a three-dimensional coordinate system, such as a Cartesian, cylindrical, or spherical coordinate system, with respect to the external frame 110.

The transceiver cavity 216 can include a mark, such as a witness mark in the transceiver cavity 216 or in proximity to the transceiver cavity 216, from which the removable component can be referenced, such as to precisely locate the removable component with respect to the transceiver cavity 216. The transceiver cavity 216 can include a scale, such as to aid a user to define a fixed position with respect to the external frame 110. The scale can be located close to the transceiver cavity 216 and can include gradations, such as hash marks, arrows, alpha numeric or numeric symbols, or other indicia. In an example, the scale can be located about the periphery of the transceiver cavity 216, such as to provide a reference point to allow a user to orient a transceiver assembly 120 with the scale, such as at a desired position with respect to the external frame 110 in a repeatable fashion.

In an example, the transceiver cavity 216 can include any shape without altering the effect of the transceiver cavity 216, such as a square, a triangular, an oval, or any bilaterally or non-bilaterally symmetric or other shape. In an example, as shown in FIG. 2A, the transceiver cavity 216 can include a generally circular shape.

The external frame 110 can include a pylon 218, such as for attaching a prosthesis component to the external frame 110. In an example, the pylon 218 can be configured for a human limb, including arms, such as transhumeral and transradial prosthetics, or legs, such as transfemoral and transtibial prosthetics. The pylon 218 can be attached to the external frame 110, such as the pylon 218 can be removably attached to the external frame 110 or permanently affixed to the external frame 110.

Figure 3A:
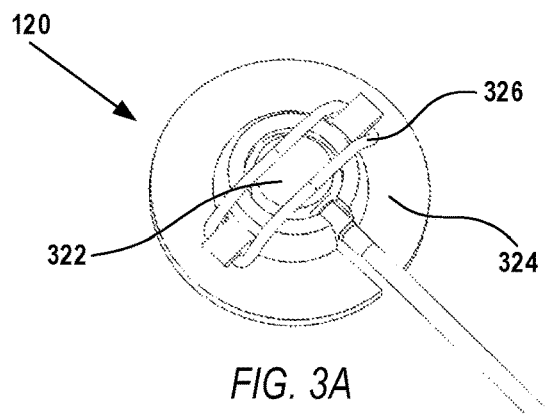
FIG. 3A shows an isometric view of an example transceiver assembly.

FIG. 3A shows an isometric view of an example transceiver assembly 120. In an example, the transceiver assembly 120 can include a transceiver device 322, a housing 324, and a retainer 326.

The transceiver device 322 can include at least one of an emitter component and a receiver component. The transceiver device 322 can generate a signal. In an example, the emitter component, such as a capacitive or piezoelectric emitter, can respond to an electrical signal applied to the emitter component, such as to convert electrical energy into mechanical energy including a pulse of mechanical energy. A mechanical energy pulse can propagate as compressive waves, such as compressive waves at sonic or ultrasonic frequency ranges, for transmission through an elastic medium, such as the bodily tissue of a patient. In an example, the transceiver device 322 can emit mechanical energy pulses, such as for transmission into a patient 105, can receive mechanical energy pulses, such as receiving reflected mechanical energy pulses from a patient 105, or can both emit and sense mechanical energy pulses.

The transceiver device 322 can include a commercially available transceiver, such as an ultrasound emitter, an ultrasound receiver, or an ultrasound transceiver, such as can include an ultrasound emitter and an ultrasound receiver. In an example, the transceiver device 322 can include a transceiver axis 337, such as a transceiver axis 337 that can be generally parallel with at least one of the direction of energy emitted from the transceiver device 322 and the direction of energy received by the transceiver device 322.

Figure 3B:
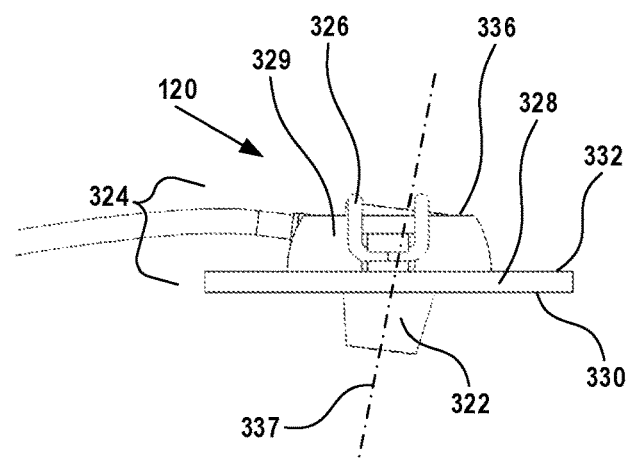
FIG. 3B shows a side view of an example transceiver assembly.

FIG. 3B shows a side view of an example transceiver assembly 120, including a housing 324. The housing 324 can include a base 328 and a cap 329 attached to the base 328, such as to support or otherwise locate a transceiver device 322 on the prosthetic external frame 110, such as to locate the transceiver device 322 with respect to the patient 105. The base 328 can include a first base surface 330, and a second base surface 332 generally parallel to the first base surface 330. In an example, generally parallel can include a configuration in which an angle formed between the first base surface 330 and the second base surface 332 varies in a range about 0 degrees, such at −1 degree to +1 degree. The cap 329 can include a cap surface 336 generally parallel to the second base surface 332. In an example, the cap surface 336 can include a solid surface, such as a contiguous solid surface, or can include a membrane with an opening, such as a hole, in the cap surface 336.

The housing 324 can include any shape without altering the effect of the housing 324, such as a square, a triangular, an oval, or any bilaterally or non-bilaterally symmetric or other shape. As shown in FIG. 3A, the housing 324 can include a generally circular shape. In an example, the shape of the housing 324 can generally conform to the shape of the transceiver cavity 216. In an example, the shape of the housing 324 can generally conform to the outer surface 214 of the external frame 110. For example, where the external frame 110 can present a generally cylindrical outer surface 214, the first base surface 330 can assume a generally curved shape to generally conform to the outer surface 214 of the generally cylindrical external frame 110.

The housing 324 can be constructed from natural or man-made materials, such as wood, plastic, or other types of material. In an example, the material selected to construct the housing 324 can include characteristics beneficial to the function of the housing 324, such as strength, rigidity, moldability, and density. For example, the housing 324 can be formed from nylon or other similar aliphatic or semi-aromatic polyamides, such as to conform with the outer surface 214 of the external frame 110.

Figure 3C:
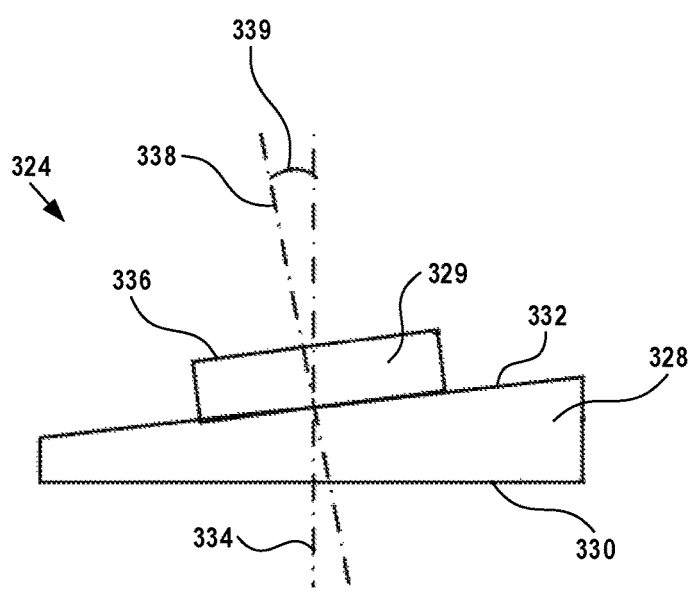
FIG. 3C shows a side view of an example transceiver assembly including an inclined base.

FIG. 3C shows a side view of an example housing 324. The housing 324 can include a base 328 and a cap 329 attached to the base 328. In an example, the base 328 can include a first base surface 330, a second base surface 332 not generally parallel to the first base surface 330, and a base axis 334 generally perpendicular to the first base surface 330. In an example, the cap 329 can include a cap surface 336 generally parallel to the second base surface 332 and a cap axis 338 generally perpendicular to the cap surface 336.

In an example, the base axis 334 and the cap axis 338 can form an angle 339, such as the cap axis 338 can form a non-zero angle 339 with the base axis 334. The angle 339 can include any value from approximately 0 degrees to approximately 180 degrees, such as 1 degree, 2 degrees, 5 degrees, 10 degrees, 20 degrees, 50 degrees, or other number of degrees. For example, as shown in FIG. 3C, the angle 339 can include a value of approximately 7 degrees. In an example, including an angle 339 in the housing 324 can allow a user a wider range of view to improve signal fidelity, such as signal fidelity associated with a strong rest-position signal.

Figure 4:
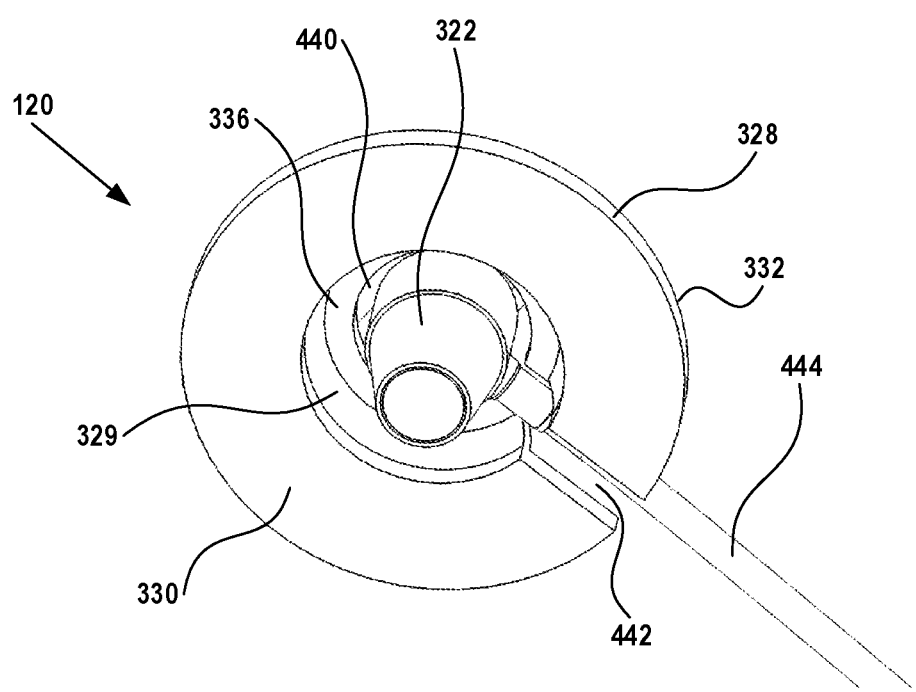
FIG. 4 shows a bottom view of an example transceiver assembly.

FIG. 4 shows a bottom view of an example transceiver assembly 120. In an example, the transceiver assembly 120 can include a cap surface 336 with a hole 440, such as to receive a transceiver device 322, and a gap 442, such as can extend from the first base surface 330 to the second base surface 332. In an example, the gap 442 can extend from the base 328 to the cap 329, such as to provide a clear space to locate a cable 444 attached to the transceiver device 332.

Figure 5A:
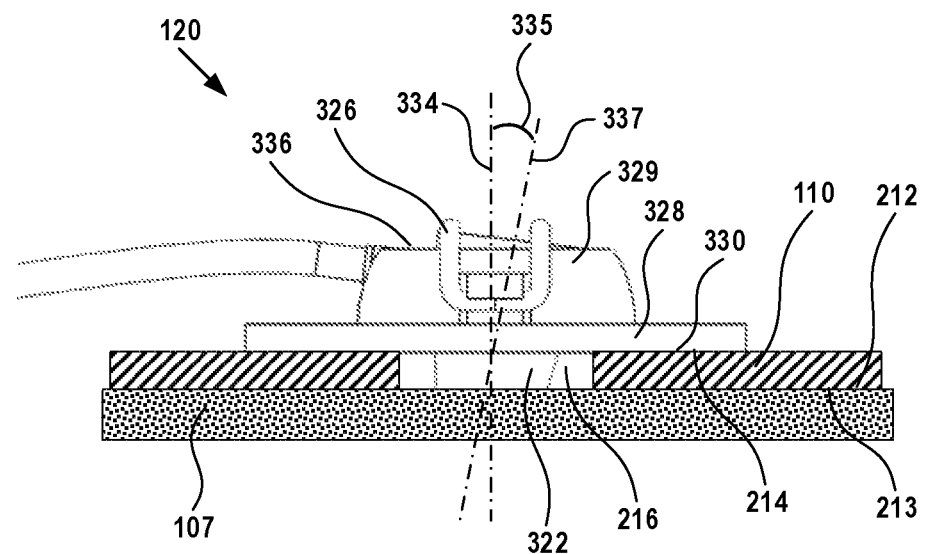
FIG. 5A shows a section side view of an example transceiver assembly positioned in a transceiver cavity, such that the transceiver assembly can be in contact with the dermis of the residual limb.

FIG. 5A shows a section side view of an example transceiver assembly 120 positioned in a transceiver cavity 216, such that the transceiver assembly 120 can be in contact with the dermis of the residual limb 107. In an example, the interface surface 213 can be formed between the inner surface 212 of the external frame 110 and the dermis of the residual limb 107. The transceiver assembly 120 can be attached to the external frame 110. For example, the first base surface 330 of the base 328 can be attached to the outer surface 214 of the external frame 110, such as with an adhesive. The transceiver assembly 322 can extend through the transceiver cavity 216, such as to contact the dermis of the residual limb 107. In an example, the retainer 326 can contact the transceiver assembly 322, such as to apply a force to the transceiver assembly 322, such as to cause the transceiver assembly 322 to be pressed against the dermis of the residual limb 107.

The transceiver device 322 can be in contact with the cap 329 such that the transceiver device 322 can maintain a position with respect to the cap 329. The transceiver device 322 can be retained against the cap 329 with a retainer 326, such as a device that can extend between the transceiver device 322 and the cap 329. In an example, a retainer 326 can include at least one of a latch, a friction lock mechanism, or a fastener, such as a set screw. In an example, the retainer 326 can be elastic, such as a pliable membrane or a spring. For example, the retainer 326 can include an elastic loop, such as a rubber band, as shown in FIG. 5A.

The retainer 326 can locate the transceiver device 322 with respect to the housing 324. In an example, the retainer 326 can apply force to the transceiver device 332, such as force sufficient to maintain the location of the transceiver device 332 with respect to the housing 324. For example, the transceiver device 322 can be located, such as in contact with the cap 329 and the patient 105, so that the transceiver axis 337 can form an angle with respect to the base 328, such as an angle 335 defined with respect to the base axis 334, in which the retainer 326 can maintain the angle 335, such as when the patient 105 moves during physical activity.

The retainer 326 can apply force to the transceiver device 322, such as force sufficient to cause the cap surface 336 to deflect and press the transceiver device 322 into the residual limb 107. The force generated by the retainer 326 can maintain a user-defined position of the transceiver device 332 with respect to the cap 329, such as through friction generated between the transceiver device 332, the cap surface 336, and the residual limb 107. In an example, the transceiver device 322 can be adjusted with respect to the base 328, such as to vary the angle 335.

The housing 324 can support the transceiver device 322, such that the transceiver device 322 can be located at a defined position with respect to the housing 324. The housing 324 can be located in the transceiver cavity 216 such as to locate the transceiver device 322 at a fixed position with respect to the external frame 110. For example, the housing 324 can be located in the transceiver cavity 216, such as the housing 324 can maintain a fixed position with respect to the external frame 110. The housing 324 can include a scale, such as to assist in defining a fixed position with respect to the external frame 110. For example, the housing 324 can be located in the transceiver cavity 216, rotated so that the housing 324 aligns with the scale, such as a particular direction on the scale, and secured to the transceiver cavity 216, such as with friction between the housing 324 and the transceiver cavity 216, such as to define a fixed position of the housing 324 with respect to the external frame 110.

The housing 324 can be attached to the external frame 110 such that the housing 324 can maintain a permanent position with respect to the external frame 110. For example, the housing 324 can be located in the transceiver cavity 216, rotated so that the housing 324 aligns with the scale, such as a particular direction on the scale, and secured to the transceiver cavity 216 with an adhesive, such as a bonding agent including an epoxy or tape, to attach the housing 324 to the external frame 110.

Figure 5B:
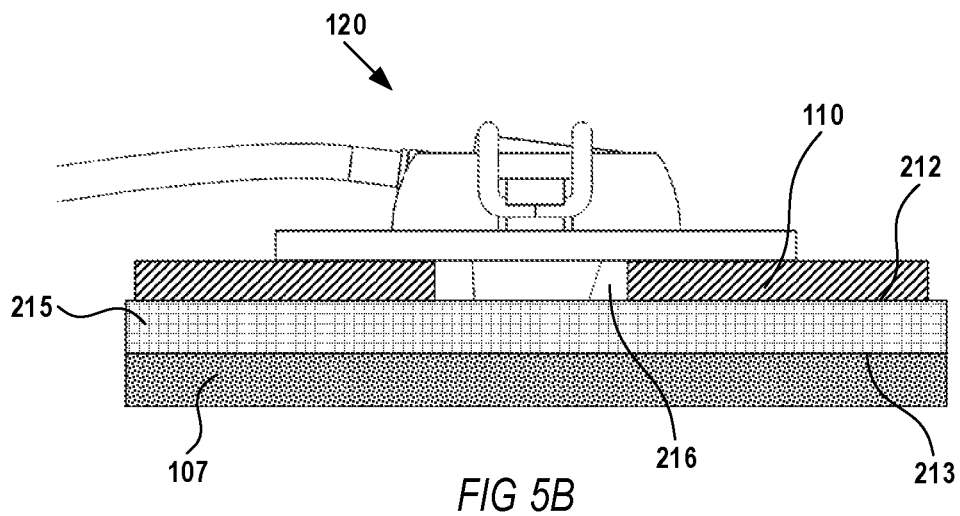
FIG. 5B shows a section side view of an example transceiver assembly positioned in a transceiver cavity, such that the transceiver assembly can be in contact with the liner.

FIG. 5B shows a section side view of an example transceiver assembly 120 positioned in a transceiver cavity 216, such that the transceiver device 322 can be in contact with the liner 215. In an example, a surface of the liner 215 can be in contact with the external frame 110, such as the inner surface 212, and the surface of the liner 215 opposite the inner surface 212 can be in contact with the dermis of the residual limb 107, such as to form the interface surface 213.

Figure 6:
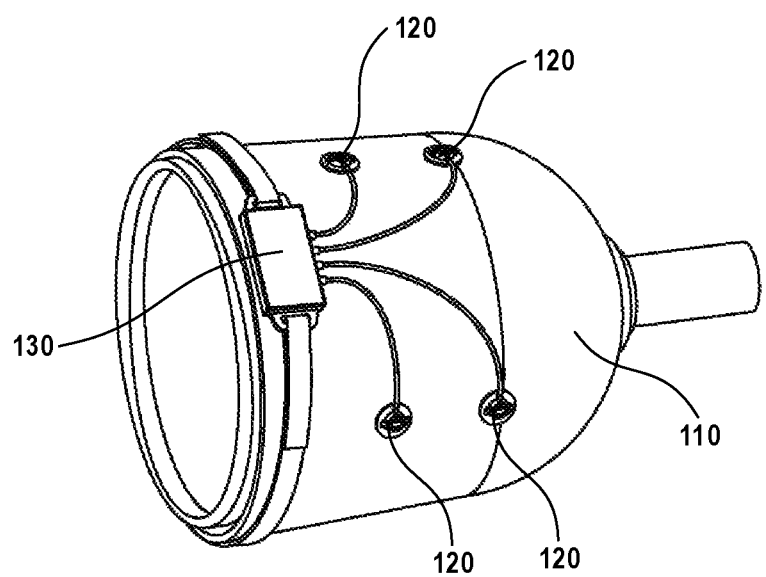
FIG. 6 shows an example of a processing module attached to an example socket shell.

FIG. 6 shows an example processing module 130 attached to an example external frame 110. The one or more transceiver assemblies 120 can be connected to the processing module 130, such as the one or more transceiver assemblies 120 can be in electrical communication with the processing module 130. In an example, electrical communication can include a wired connection, such as the transceiver assembly 120 and the processing module 130 can be connected by a wire to enable electrical communication. In an example, electrical communication can include wireless communication capabilities, such as the transceiver assembly 120 can communicate with the processing module 130 via a wireless connection.

The processing module 130 can include a microcontroller, such as a PIC-type microcontroller including a PIC module. The microcontroller can perform data processing functions, such as data logging, data filtering and weighting, and data transmission. The processing module 130 can be in electrical communication with an external electronic device, such as a personal computer (PC), or mobile device, such as a tablet computer and a smart phone.

Figure 7:
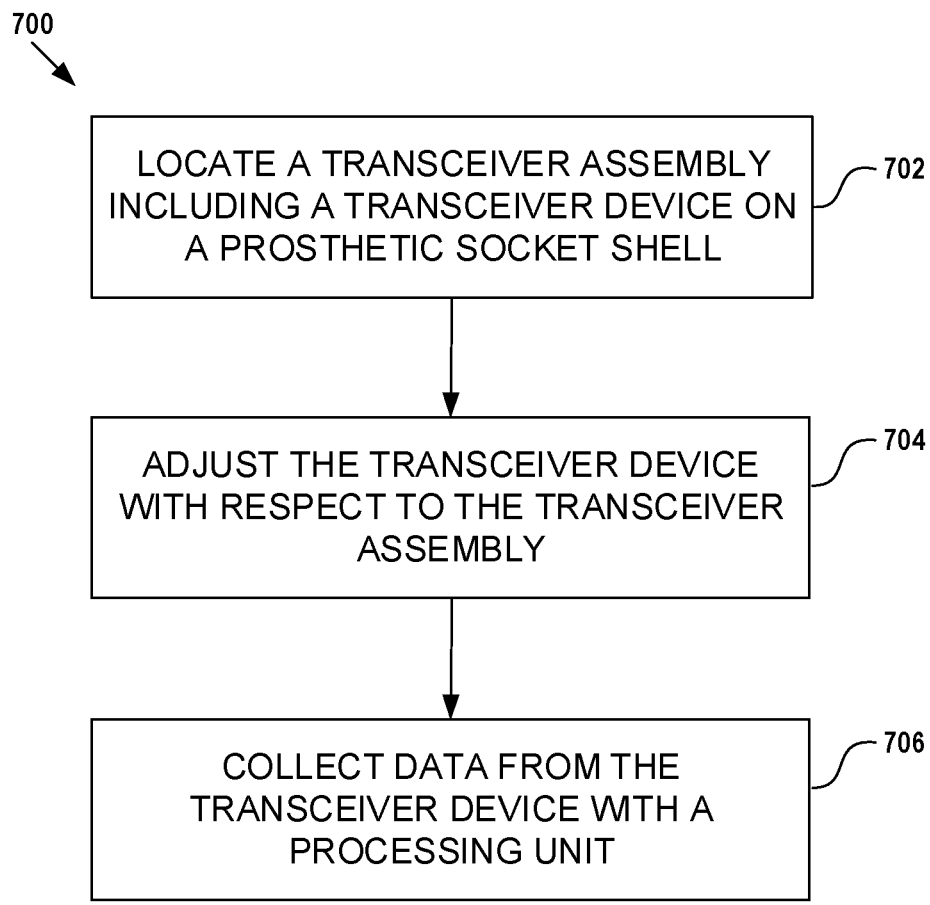
FIG. 7 shows an example of a method to use a prosthetic socket fitment system.

FIG. 7 shows a flow diagram of an example method 700 of using a prosthetic socket fitment system 100. The method 700 can be applied to a prosthesis or prosthesis component, such as a external frame 110. In an example, the external frame 110 can include one or more transceiver cavities 216.

At 702, a transceiver assembly 120 including a transceiver device 322 can be located on a prosthetic external frame 110, such as to collect information from a grid of measurement locations. The grid of measurement locations can be defined by one or more coordinate systems, such as one or more coordinate systems referenced from the transceiver assembly 120.

Locating a transceiver assembly 120 can include providing a transceiver assembly 120, such as a transceiver assembly 120 with an ultrasonic transceiver device. In an example, the transceiver assembly 120 can include a dual element ultrasonic transceiver, such as a transceiver in which two angled, crystal elements create a v-shaped mechanical energy pulse path. For example, a first angled crystal element can act as an emitter, a second angled crystal element can act as a receiver, and an acoustic barrier can separate the first and second angled crystal elements Locating a transceiver assembly 120 can include locating the transceiver assembly 120 on the external frame 110, such as to establish a strong rest-position signal. In an example, a strong rest-position signal can include a position of the transceiver assembly 120 with respect to the external frame 110 that can result in receiving the largest magnitude transceiver signal, such as a transceiver signal that can be reflected from the bone of a patient. The strong rest-position signal can be established by changing the position of the transceiver assembly 120 with respect to the external frame 110, such that the user can identify the position, such as the orientation of the assembly 120 with respect to the external frame 110, from which the largest transceiver signal can be received. For example, the position of the transceiver assembly 120 can be changed, such as by at least one of rotating the transceiver assembly 120 from a first rotation position to a second rotation position with respect to the scale and by moving the transceiver axis 337 of the transceiver device 322 from a first angle position to a second angle position, such as to locate an optimum strong rest-position signal. In an example, an audio response from a visualization program can help establish the signal level, such as a strong rest-position signal level, without requiring visual attention.

Locating a transceiver assembly 120 can include attaching the transceiver assembly 120, such as to the external frame 110. The housing 324 can be affixed to the external frame 110 with an adhesive, such as double-stick-tape or one-minute epoxy. In an example, the retainer 326 can press against the transceiver device 322 with a holding force such that the cap surface 336 can flex in reaction to the holding force. For example, the transceiver device 322 can maintain a specified position with respect to the cap surface 336 due to the holding force imposed by the retainer 326 such as by friction generated between the transceiver device 322 and the cap surface 336.

At 704, the transceiver device 322 can be adjusted with respect to the transceiver assembly 120, such as to collect information from a grid of measurement locations. The grid of measurement locations can be defined by one or more coordinate systems, such as one or more coordinate systems referenced from the transceiver assembly 120.

A coordinate system can include a roll coordinate system, such as a cylindrical coordinate system referenced from an axis perpendicular to the plane formed by the base axis 334 and the transceiver axis 337, such as the roll axis. The roll coordinate system axis can be located at the intersection of the base axis 334 and the transceiver axis 337, such as shown in FIG. 5A. The transceiver device 322 can be accurately located in the roll coordinate system with respect to the prosthetic external frame 110, such as by attaching an angle measuring device including a protractor to the transceiver device 322, aligning delineations on the protractor with the transceiver axis 337, and rotating the transceiver device 322 about the roll axis, such as to vary the angle 335. In an example, the transceiver device 322 can be located by rotating the transceiver axis 337 from a first position, such as a first roll position, to a second position, such as a second roll position.

A coordinate system can include a base coordinate system, such as a cylindrical coordinate system in a plane perpendicular to the base axis 334. The base coordinate system can be delineated with a scale, such as the scale located on the housing 324 of the transceiver assembly 120. The transceiver assembly 120 can be located, such as accurately located, in the base coordinate system with respect to the prosthetic external frame 110, such as by orienting the scale on the housing 324 to the witness mark in proximity to a transceiver cavity 216. In an example, the transceiver device 322 can be located with respect to the base coordinate system, such as by rotating the transceiver assembly from a first position, such as a first rotation position in the base coordinate system, to a second position, such as a second rotation position in the base coordinate system.

Adjusting the transceiver device 322 can include adjusting the transceiver device 322 in one or more coordinate systems, such as one or more coordinate systems that define a grid of measurement locations. In an example, the transceiver device 322 can be rotated with respect to one or more coordinate systems, such as a base coordinate system and a roll coordinate system, such as to steer the field of view of the transceiver device 322 to identify a strong rest-position signal, such as a strong bone echo. The strong rest-position signal can be defined by a set of coordinate locations, such as a base angle and a roll angle. The transceiver device 322, such as the transceiver device 322 located at a set of coordinate locations defining a strong rest-position signal, can be affixed to the transceiver assembly 120, such as to maintain the strong rest-position signal, with a retainer 326.

At 706, data can be collected from the transceiver assembly 120, such as the transceiver device 322, with a processor, such as the processing unit 130. Collecting data from the transceiver device 322 can include generating compressive waves with the transceiver device 322, such as for transmission through an elastic body including bodily tissue of the patient. Generating compressive waves can include generating an electrical signal, such as at least one of an electrical current and an electrical voltage that varies with time, with an electronic device, such as at least one of a microcontroller including a microcontroller located in the processing unit 130 and an external electronic device. The electrical signal can be transmitted from the electronic device through the processing unit 130 to the transceiver device 322, such as the emitter component of the transceiver device 322 located against the tissue of the patient. The emitter component, such as a capacitive or piezoelectric emitter, can respond to the electrical signal, such as to convert electrical energy into mechanical energy, such as compressive waves including a pulse of mechanical energy, for transmission through the bodily tissues of the patient.

Collecting data from the transceiver device 322 can include receiving compressive waves, such as compressive waves reflected from a structure in the bodily tissues of a the patient including bone tissue, with the transceiver device 322, such as the receiver component of the transceiver device 322.

The collected data can relate to a physical property, such as the distance from the transceiver device 322 to a distant object. For example, the transceiver device 322 can include an ultrasonic transceiver that can be positioned relative to the residual limb 107 of the patient 105 such that data from the ultrasonic transceiver can include information about the relative distance from the ultrasonic transceiver to the bone of the patient 105. In an example, unknown quantities, such as the speed of sound in tissue and interfacial backscatter can be normalized from the data obtained from the transceiver device 322, such as through filtering and thresholding.

The received signal at the transceiver device 322, such as from the bone of the patient 105, can take the form of an unrectified acoustic amplitude, such as can be referenced in time from the start of the ultrasound burst. In an example, the transceiver device 322 can include an embedded microcontroller to generate mechanical energy pulses, such as sonic and ultrasonic frequencies, and process data, such as data acquisition, on signals related to distance measurements. In an example, the processing module 130 can include at least one embedded microcontroller, such as to collect information regarding the fitment qualities of the external frame 110 when the patient 105 can engage in a range of physical motions.

The processing module 130 can include an embedded microcontroller. In an example, the embedded microcontroller can generate mechanical energy pulses for transceiver device 322. For example, the transceiver device 322 can include an ultrasonic transceiver that can generate ultrasonic pulses at a frequency greater than 1 kilohertz. In an example, data can be collected by the transceiver device 322. For example, the transceiver device 322 can include an ultrasonic transducer that can collect data, such as reflected ultrasonic pulses, and process the data, such as by rectifying, filtering, thresholding and integrating the data.

In an example, collected data can be processed such as to provide an estimate of distance from the transceiver device 322 to the bone of the patient 105. In an example, the collected data from each transducer can be rectified and filtered, and then thresholding and integration can be applied to precisely determine the echo time, such that the distance from the transceiver device 322 to the bone of the patient 105 can be established to within a measure of uncertainty, such as the uncertainty of the sound speed. In an example, collected data from multiple mechanical energy pulses can be averaged, such as to reduce variability in the collected data.

Collecting data from the transceiver device 322 can include transmitting received compressive waves to an external electronic device, such as transmitting the received compressive waves through the processing module 130 to the external electronic device. The at least one processing module 130 can include communication circuitry, such as to enable wireless transfer of data between electronic devices. In an example, Bluetooth® compatible circuitry aboard the processing module can be transmitted as a real-time sensor feed to the coupled PC computer. In setting the threshold, such as a minimal signal threshold for the computer, raw data sequences can be sent wirelessly and the user-set threshold can be received and applied to the threshold and integration processes on the microcontroller.

The processing module 130 can include a wireless data feed to the visualization and storage computer, which could be many meters away. In an example, two-way communication can allow the PC software to set the trigger threshold at the microprocessor, based on data packets visualized in software. In an example, other wireless data protocols, such as ZigBee, can be used in the event multiple processor boxes are required.

Collecting data from the transceiver device 322 can include processing the received compressive waves with the external electronic device. In an example, the counter. In an example, the external electronic device can include a counter, such as a device or functionality of the processing unit 130 that can calculate the time between emitting a compressive wave and receiving a reflected compressive wave, to determine a distance, such as the distance from the transceiver assembly 120 to the reflecting surface including the bone of the patient.

Processing the received compressive waves can include identifying the largest magnitude compressive wave from a set of received compressive waves, such as a set of received compressive waves collected from a grid of measurement locations associated with a transceiver assembly 120. In an example, varying values associated with the base and roll coordinate systems can define a grid of measurement locations, such as for a transceiver assembly 120. The magnitude of received compressive waves at each measurement location can vary, such as due to dissipation of mechanical energy in transmission through an elastic medium. In an example, the largest magnitude received compressive wave can indicate the shortest distance between the transceiver assembly 120 and the reflecting surface and can be interpreted as the strong (or optimal) rest-position of the transceiver assembly 120. In an example, at least one of the processing unit 130 and the external electronic device can identify the largest magnitude compressive wave from a set of received compressive waves, such as to identify the strong (or optimal) rest-position of the transceiver assembly 120.

Figure 8:
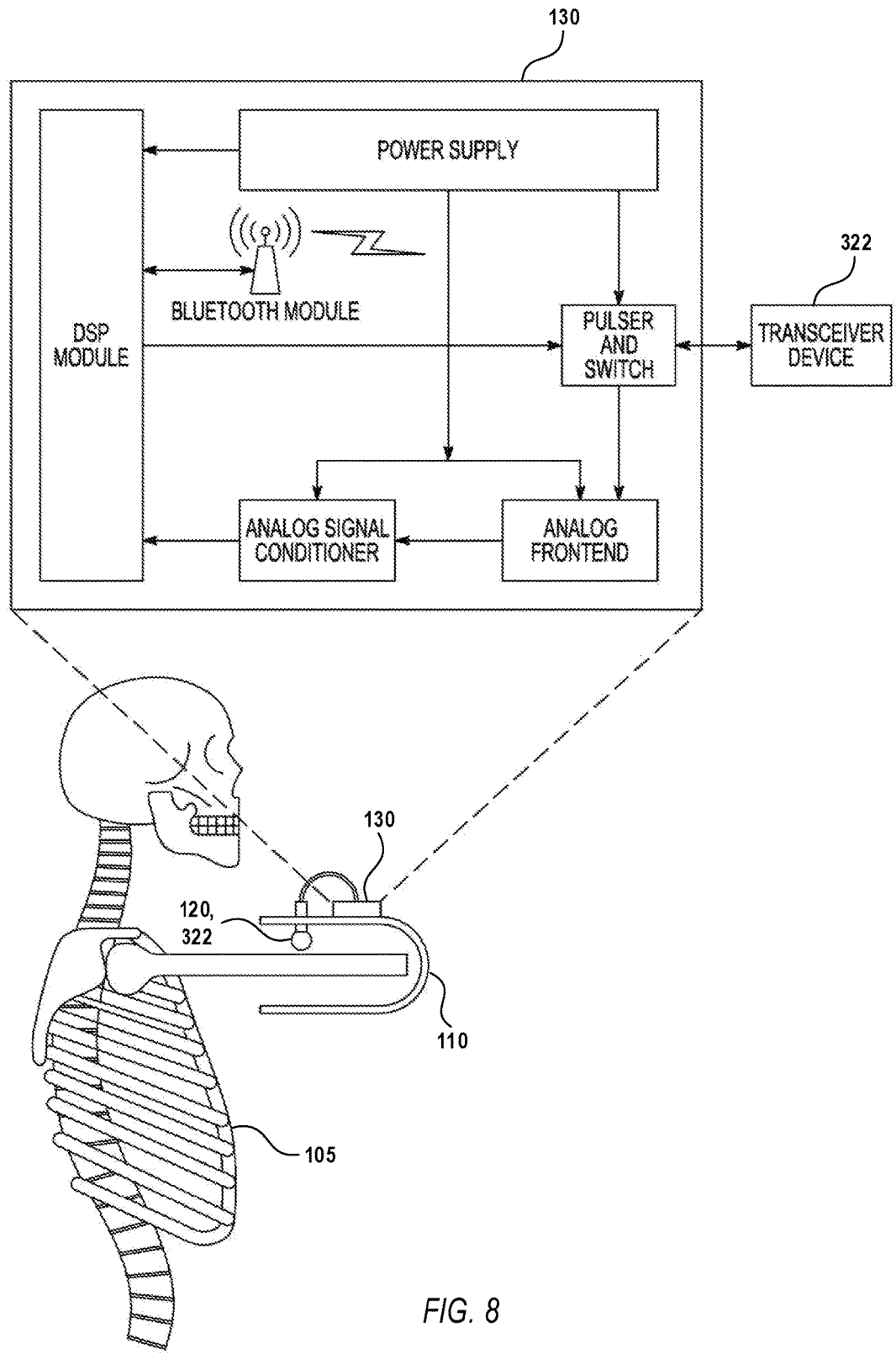
FIG. 8 shows a functional diagram of an example prosthetic socket fitment system.

FIG. 8 shows a functional diagram of an example prosthetic socket fitment system 100. The system 100 can collect data, such as quantitative data, that relates the load-bearing structures, such as the patient 105 including bones and the skeleton, and the external frame 110. The collected data can enhance prosthesis fitting procedures, such as data-driven cast modifications, such as to monitor and evaluate fit of the prosthesis including the external frame 110 to the patient 105 over time. The system 100 can enhance existing prosthesis fitting procedures, such as to improve patient comfort and satisfaction of the prosthesis. The system 100 can include software, such as processing algorithms and graphical user interfaces (or GUIs), which can be run on a computer, such as a PC, a laptop, a tablet computer, and a PIC module. In an example, the system 100 can use an observation method, such as ultrasound including an amplitude mode (or A-Mode) observation method, to enhance existing prosthesis fitting procedures, such as data-driven cast modifications.

In an example, a transceiver assembly 120 including a transceiver device 322, such as an ultrasonic transceiver, can be located on an external frame 110, such as to measure orientation of a bone of a residual limb 107 with respect to the external frame 110. A connection, such as an electrical connection, can be made between the transceiver device 322 and a processing module 130, such as with a coaxial cable. Signal processing, such as calculating bone motion relative to the external frame 110, can be performed on the processing module 130 and transmitted to an external electronic device, such as for post-processing including display of the processed signals. Calculating bone motion relative to the external frame 110 can include use of the transceiver device 322, such as determining the time between emitting a mechanical energy pulse from the transceiver device 322 and receiving a reflected mechanical energy pulse with the transceiver device 322. In an example, signal processing can be performed and post-processed on the external electronic device. In an example, the system 100 including the processing module 130 and the transceiver device 322, can be battery powered and portable.

Referring to FIG. 8, the processing module 130, can include multiple modules, such as at least one of a power supply module, a pulser & switch (or PS) module, an analog front-end (or AFE) module, an analog signal conditioning (or ASC) module, a communications module including a wireless transmission unit, and a digital signal processing (or DSP) module.

The power supply module can provide all the necessary regulated voltages from a 9 V battery, such as to power all modules attached to the processing module 130. The power supply module can provide voltage to the processing modules 130, such as voltages including 5 V, −5V, 3.3 V, and 60V-100V. In an example, voltage for the PS module can include voltage generated by using a pulse-width modulation (PWM) based boost converter adjustable from 60 V to 100V, such as with a potentiometer.

The PS module can control the mechanical energy pulse generated by the transceiver device 322, such as a transceiver device electrically connected to the PS module. The PS module can generate a logic control signal, such as a voltage that can vary with time, which can be converted by the transceiver device 322 into a mechanical energy pulse for transmission into the patient 105. The PS module can include a high voltage channel, such as a channel including capability of ±70 volts, and a damping unit, such as a damping unit with one or more FET components, which can power and excite a transceiver device 322, such as a single-element ultrasound transducer, according to a logic control input. In an example, the PS module can include a switch, such as a transmit and receive switch, which can protect the PS module, such as by electrically isolating the PS module including a low noise receiver up to ±130 V.

The AFE module can receive information, such as received signals, from the transceiver device 322. The AFE module can include eight (8) input channels and can amplify received signals, such as reflected ultrasound signal, with built-in low noise amplifiers. The gain of the amplifiers can be adjusted and controlled, such as adjusted and controlled by using signals including related inputs from the AFE module, such as to provide one or more differential analog outputs, such as to keep the signal to noise parameters low. The AFE module can achieve a noise threshold, such as an ultra-low 2.4 dB noise threshold at with an input resistance of 200Ω.

The ASC module can condition a received signal. In an example, the ASC module can change an output, such as a differential output, to a different output, such as a single ended output, such as to condition a received signal including a reflected ultrasound signal, for the DSP modules, such as a digital input of the DSP module.

The communications module, such as a Bluetooth module, can establish electronic communication between the DSP module and an external electronic device, such as a device running a GUI. The communications module can include an embedded Bluetooth stack, such as to support multiple interface protocols and profiles including the commonly used SPP and HID profiles. The communications module can be integrated into the processing module 130, such as through a UART serial data interface. The communications module can control all the process within the processing unit 130. In an example, the communication module can include a PIC-type microcontroller, such as a microcontroller from the PIC 32 MZ family from Microchip Technology (Chandler, Ariz.). For example, the communication module can include a chip, such as a chip with a 32-bit architecture running at 200 MHz, a 12 bit A/D converter operating 48 channel supporting 18 MSPS with 9 input capture units, 2048 KB Flash, and 512 KB RAM.

The transceiver device 322, can generate mechanical energy and sense or otherwise receive mechanical energy. The transceiver device 322 can include a transducer, such as a single element ultrasonic transducer. A single element ultrasonic transducer can include a single crystal element housed in a casing. The single crystal element can both transmit and receive energy, such as mechanical energy transferred with compressive waves at ultrasonic frequencies. In an example, the transceiver device 322 can include a single element ultrasonic transducer, such as a transducer with a nominal frequency of about 2.25 MHZ and a diameter of approximately 0.635 cm.

The transceiver assembly 120 can support the transceiver device 322, such as to locate the transceiver device 322 with respect to the external frame 110. The transceiver device 322, such as an ultrasonic transceiver device, can emit (or otherwise drive to generate) mechanical energy at a specific frequency, such as a resonant frequency of the ultrasonic transducer. For example, the ultrasonic transceiver device 322 can be activated with a voltage pulse, such as a voltage pulse of about 60 volts for a duration (or pulse width) of approximately 450 nanoseconds, generated by processing module 130, such as the PS module. The ultrasonic transceiver device 322 can be activated by multiple voltage pulses, such as multiple voltage pulses separated by approximately 40 milliseconds, the multiple voltage pulses generated by an integrated circuit, such as a pulser integrated circuit that can be controlled by the DSP module. The multiple voltage pulses can be directed into a patient 105, such as a residual limb 107 of a patient 105.

The transceiver device 322 can receive reflected mechanical energy, such as compressive waves emitted by the transceiver device 322 and subsequently reflected from the bone of a residual limb 107. The reflected wave can generate a signal, such as the transceiver device 322 can convert the reflected compressive waves into an electrical signal including a reflected signal. The AFE circuit can provide amplification of the reflected signal, such as with at least one of a low-noise amplifier (LNA) and a variable-gain amplifier (VGA) including an anti-alias filter (AAF). The reflected signal can be isolated, such as electrically isolated, from the PS module, such as to protect the AFE circuit from high voltages. In an example, the gain of the LNA can be set, such as by programming bits as 12.5 decibel or 18.5 decibel. The gain of the variable gain driver (VGA) can be adjusted through differential gain control inputs, such as by using a digital-to-analog converter (DAC) electrically connected to the VGA. In an example, the VGA gain can be set, such as between 3 decibel and 35 decibel. The connection, such as the electrical connection between DSP and DAC can be established through a serial bus, such as an I²C (or inter-integrated circuit) serial bus protocol at 400 kbits.

The AFE circuit can provide an output. A differential to single-ended line receiver can be used for converting the output of the AFE, such as a differential output, to a single ended output, such as for analog signal conditioning. In an example, the reflected signal, such as a reflected analog signal, can be converted to logic pulses, such as to directly apply the reflected signals as an input capture unit of the DSP module. The input capture unit of the DSP module can apply a filter, such as a threshold-based filter, to the reflected analog signal received by the input capture unit. In an example, the threshold-based filter can be described with the following function:

$$y(t) = \begin{cases} \text{logic1} & \text{if } s(t) \geq TVL \\ \text{logic0} & \text{if } s(t) < TVL \end{cases}$$

In an example, the variable t can include time, the variable s(t) can include the received reflected analog signal as a function of time, the variable y(t) can include the output of the threshold-based filter, such as a logical output, as a function of time, and the variable TVL can include the threshold voltage level. In an example, the TVL can be adjusted, such as with a potentiometer.

Figure 9:
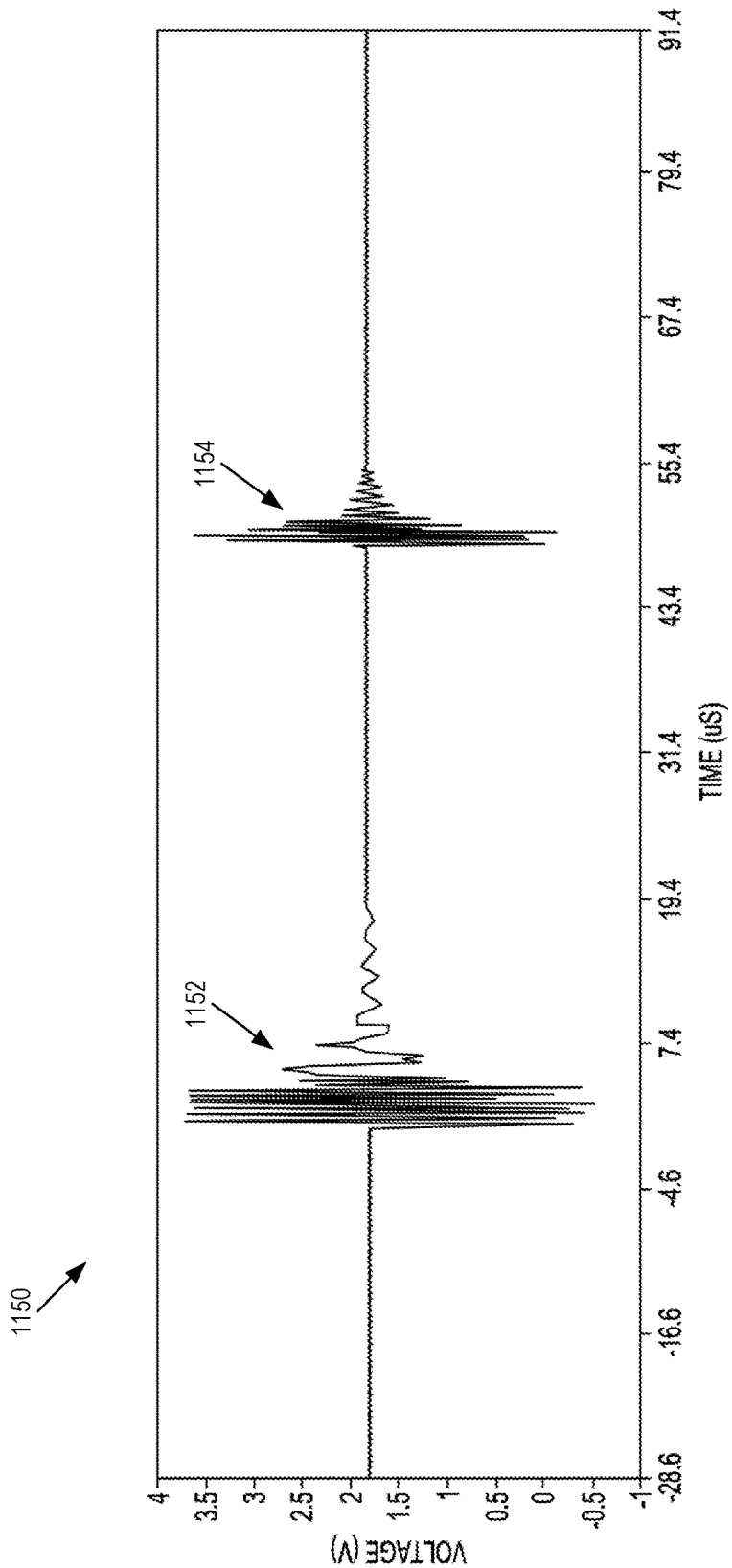
FIG. 9 shows an example time history generated by a transceiver device.

FIG. 9 shows an example time history 1150 generated by a transceiver device 322. The time history 1150 can include a first pulse region 1152, such as an emitted pulse of mechanical energy generated by the transceiver device 322, and a second pulse region 1154, such as a reflected pulse of mechanical energy received by the transceiver device 322. The second pulse region 1154 can be dependent on the first pulse region 1152. In an example, the first pulse region 1152 can be transmitted into a residual limb 107 by an emitter of the transceiver device 322, such as the first pulse region can impinge upon the bone of the residual limb 107, and reflected from the bone of the residual limb 107 as the second pulse region 1154, such as the second pulse region 1154 can return through the residual limb 107 to a receiver of the transceiver device 322.

The difference in time between the first pulse region 1152 and the second pulse region 1154 can have a physical significance. In an example, the time difference between the first and second pulse regions 1152, 1154 can be related to the distance between the outer surface of the dermis of a patient 105 and the bone of the residual limb 107, such as the thickness of the tissue between the outer surface of the dermis and the bone. The thickness of the tissue can be related to the propagation speed with which mechanical energy, such as a compressive wave, can be transmitted through the tissue of the residual limb 107. In an example, the thickness of tissue can be calculated with the following equation:

$$D = \tfrac{1}{2} vt$$

In an example, the variable v can include the propagation velocity of the mechanical compressive wave in the tissue, the variable t can include time, such as the time between the first and second pulse regions 1152, 1154, and the variable D can include the thickness of the skin, such as half of the total distance traveled by the impinging and reflected compressive waves recognizing that the total distance traveled (i.e., the distance from the surface of the dermis to the reflecting bone back to the surface of the dermis) can be twice the thickness of the tissue.

The DSP module can control functional operation of the system 100. In an example, functional operation can include multiple discrete operations, such as at least one of initiating the PS module, storing of collected data, such as representations of the first and second pulse regions 1152, 1154, and transmitting the collected data to a processing unit, such as to at least one of a mathematical processing function of the DSP module and an external electronic device.

Initiating the PS module can include triggering the input capture unit, such as with transistor-transistor logic (or TTL) pulses to collect data. The TTL pulse can be related to an external stimulus of the system 100, such as the push of a button by a user of the system 100, or an internal stimulus, such as at least one of a timer integral to the DSP module configured to generate a TTL pulse at regular intervals and a switch integral to the DSP module configured to generate a TTL pulse on the occurrence of a specified event, such as receiving a second pulse region 1154 at a transceiver device 322. In an example, the DSP module can include multiple input capture units, such as nine (9) input capture units, and multiple digital timers, such as nine (9) digital timers.

An image capture unit can include a digital input, such as a binary electrical switch, to indicate that signal has changed from a first level to a second level. In an example, the image capture unit can include a portion of the DSP module memory, such as a 1 bit binary register, otherwise known as a flip-flop.

A digital timer can include a device that monitors elapsed time, such as the elapsed time between a first event and a second event. In an example, a digital timer can include a portion of the DSP module memory, such a multi-bit binary register which can tally CPU clock cycles between initiation of a first event and completion of a second event.

Storing of collected data can include saving selected parameters in a data structure, such as an organized data structure including buffer memory, such as a first-in-first-out memory (or FIFO) buffer for retrieval and processing of the collected data at a later time. In an example, selected parameters can include at least one of the value of an image capture unit, such as a binary value, and the value of a digital timer, such as a whole number.

A stored collection of data can characterize a physical quantity, such as the thickness of tissue at a given location in a residual limb 107. In an example, an event, such as an internal or external stimulus, can generate a TTL event, such as the leading edge of a TTL pulse, to activate an image capture unit, such as to drive a binary register from a low state to a high state. For example, activating the image capture unit can cause the DSP module to record a high state as a first bit in a FIFO buffer, such as to indicate initiation of a data capture cycle, and record an initial count of CPU cycles as a second bit in a FIFO buffer, such as zero cycles at the initiation of data capture. In an example, an event, such as receiving a reflected compressive wave at a transceiver device 322, can generate a TTL event, such as the trailing edge of a TTL pulse, to deactivate the image capture unit, such as to drive the binary register from a high state to a low state. For example, deactivating the image capture unit can cause the DSP module to record a low state as a third bit in a FIFO buffer, such as to indicate completion of a data capture cycle, and record the total count of CPU cycles as a fourth bit in a FIFO buffer, such as the number of CPU cycles accumulated between the initiation and completion of a data capture cycle.

Transmitting the collected data can include passing of values in a buffer to a processing module, such as a location on the DSP module that performs at least one of logical and mathematical calculations. In an example, collected values in the FIFO buffer can be mathematically processed, such as by subtracting the second bit from the fourth bit to calculate the total CPU cycles between leading and trailing edges of the TTL pulse and the result subsequently multiplied by the length of time of one CPU cycle to determine the total time duration between leading and trailing edges of the TTL pulse. In an example, the total time duration can be multiplied by a scaled factor, such as one-half the propagation speed of mechanical waves in a given tissue sample, to calculate the thickness of the tissue sample at a particular location on the residual limb 107. For example, the minimum distance between an outer surface of the dermis of a patient 105 and the bone of a residual limb 107 can be calculated as $3.9 \times 10^{-3}$ mm if the tissue propagation speed can be taken as 1540 m/s and the total time duration between leading and trailing edges of the TTL pulse can be taken as 5 nanoseconds.

ADDITIONAL NOTES & EXAMPLES

The prosthetic socket fitment system (or PSF System) described has been developed with acceptance in prosthetist shops as the primary design consideration. Low cost and integration with current procedures can be critical parts of the proposed design. Several other design options can be included in the PSF system.

The PSF System can include active padding control. As a simple, modular sensing modality, line-of-sight ultrasonic bone movement monitoring can be an important part of advanced and adaptive prosthesis systems. Active padding control can include the ability to modify the inflation of padding to compensate for bone movement during high-load or high-speed activities, and then relax padding constriction to return comfort and circulation has great potential. The PSF System can be implemented as part of a sensor suite that includes smart fabric internal pressure sensing for additional guidance on socket padding design.

The PSF System can include a bone image reconstruction system. The bone image reconstruction system can include information necessary to guide the fitment process. In an example, additional transducers and automated inference can provide the user with a more complete view of the location, condition, and movement of the entire bone.

The PSF System can include smart exercise accessories. Smart exercise accessories can include a data feed, such as a Bluetooth data feed from one or more sensors, such as ultrasound sensors. Additional components, such as additional battery-powered Bluetooth accessories, can be used in exercises. In an example, a smart exercise accessory can include a fixed weight with a Bluetooth enabled load cell to measure g-loading during lifting or swinging operations. The load cell information can be collected by the same software, such as PSF System software, to enable visualization of data, such as synchronous visualization of instantaneous load vs. bone movement, such as to allow the socket fit to be adjusted according to the kinds of activities that are anticipated, or to enable a good balance of performance and comfort across a range of activities.

The PSF System can include a self-optimization system. In an example, PSF System data, such as ultrasound data, can be used to self-align the PSF System with servomotor mounting.

The PSF System can include PSF System Software.

Figure 10:
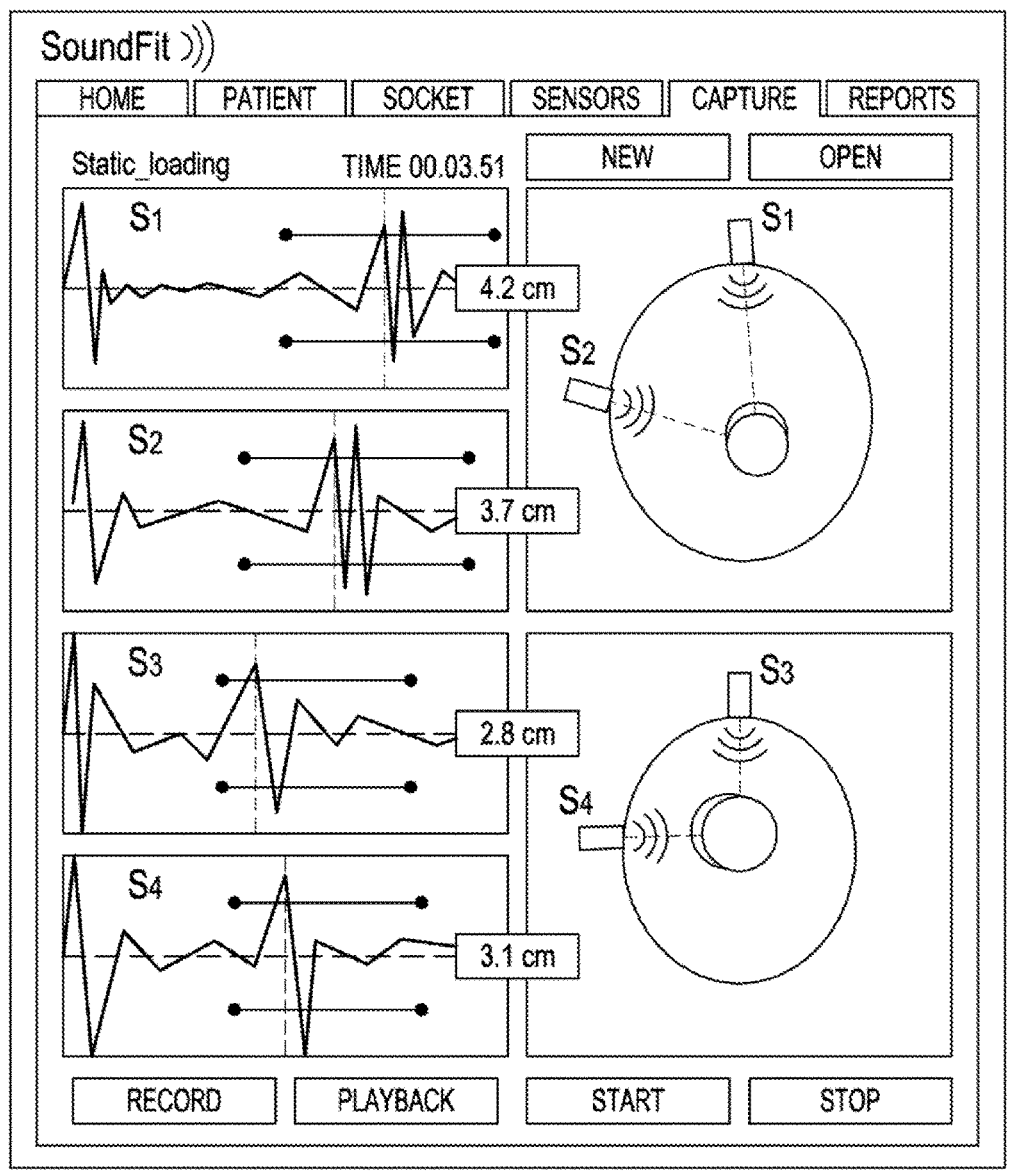
FIG. 10 shows an example of a user interface concept.

A user can gain actionable fitment information through PC software. In an example, most of the high-speed data processing can be accomplished in the PIC module, such as with only lower-bandwidth raw data transmitted by Bluetooth. The software can provide real-time readout of the bone motion detected by each sensor, such as data can be visualized according to the sensor layout (from inputs by the prosthetist), such as to provide an accurate geometric interpretation. FIG. 10 shows an example of a user interface concept. In an example, recording of movement videos corresponding to particular motions or exercises can be possible, as well as storing both videos and mean values to log files associated with each patient.

The PSF System Software can include a graphical user interface, or a GUI. As shown in FIG. 10, the interface of the PSF System software can provide a "dashboard" for viewing, recording, and reviewing bone tracking data for a particular patient. The data acquisition module can be adaptable, such as the prosthetist can input the locations of the sensors and relevant dimensions of the socket under testing. In an example, two sensors with perpendicular lines-of-sight can be defined to track x and y coordinate motions, such as both measurement points are represented in the GUI as defining semi-major and semi-minor axes of an ellipse. The actual dimensions of the socket can scale the ellipse and can be measured by the prosthetist, such as using a measuring tape, and entered into the PSF System Software, and the "rest location" can be measured and all subsequent measurements referenced to that. In an example, the bone tracking data can be at millimeter resolution. Physical measurements can help visualize the extent of the motion relative to the scale of the socket and how to improve the fit.

The PSF System can allow critical data important to the experienced prosthetist to be acquired by the technician and then presented via the GUI dashboard. In many prosthetist offices, the entire fitment process is not performed by a single person, and it is common for a "master" prosthetist to make critical examinations and final mold modifications, but for a technician to lead minor modifications, padding, testing, and education aspects of the fitment process.

Figure 11:
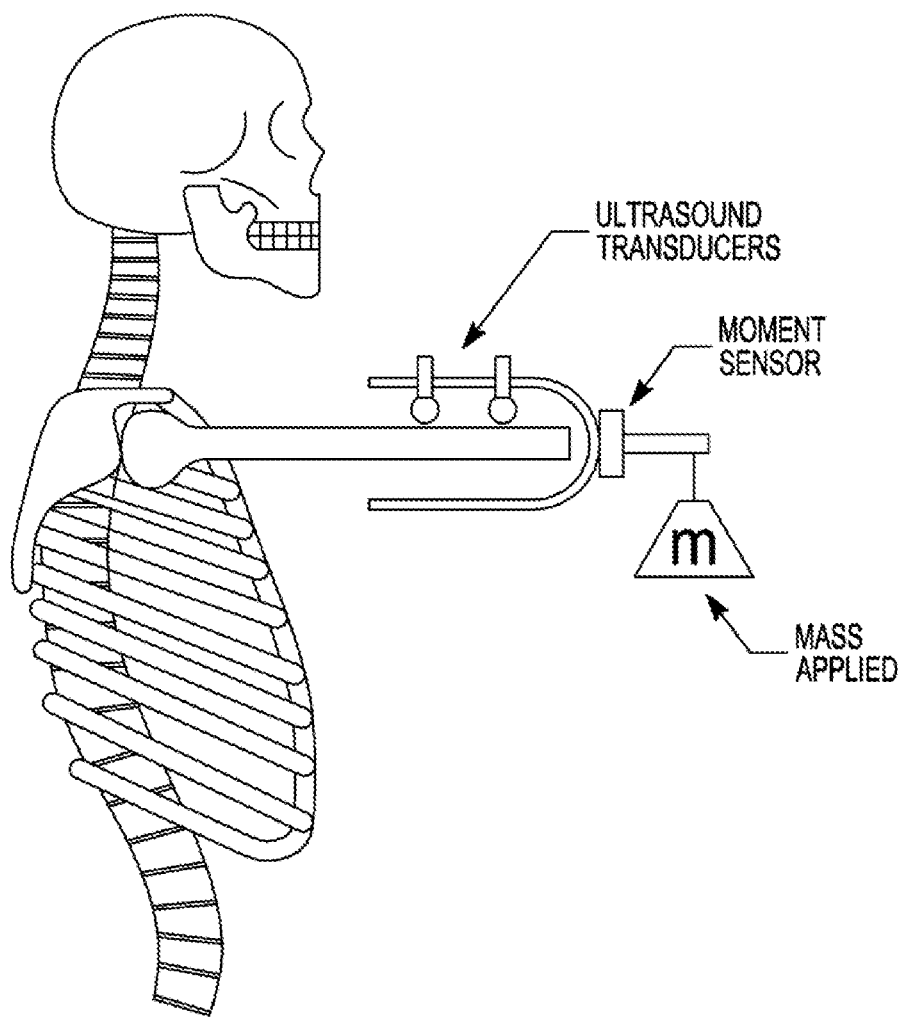
FIG. 11 shows an example of auxiliary sensors as described in the disclosure.

The PSF System Software can include exercise development function. While quantitative bone motion data can be important in the fitment process, the information can be more relevant, and can lead to more uniform fitting procedures, when coupled to specific exercises that challenge the socket fit in predictable and independent ways. In an example, it can be possible to create a fit that is very stable laterally, but fails longitudinally. Providing specific tests for each movement and saving the data for review after the exercise is performed can be an important advantage of the PSF System. In an example, data can be acquired from auxiliary sensors, such as a moment sensor as shown in FIG. 11, and displayed as part of the PSF System GUI. Sensors can include transmitters, such as active Bluetooth transmitters, or plug in modules, such as modules that can plug into auxiliary jacks in the PSF System data acquisition module. The data collected can be synchronous and simultaneous with bone movement data, such as to provide a wealth of performance data that can characterize the goodness-of-fit.

The PSF System Software can include patient profiles. As described previously, the ability to use PSF System software to monitor and trend a patient's fit history over time can be an important advantage of the system as a fully digital data source. Additional metadata relating to fit history can be stored with a patient's PSF System files, including age, residual limb dimensions, sores or lesions, level of physical activity, and so on. This can be entered by the prosthetist into the PSF System Software, such as part of a "Patient" tab as seen in FIG. 10. In the long run, it can be important for PSF System data to be compatible with other emerging electronic health record formats, and compiled as part of the overall health profile of a patient. This step can involve additional standardization and privacy measures. The PSF System software can be capable of storing information indexed by patient and include metadata from a notes field in the GUI.

The PSF System Software can include advanced concepts. The PSF System software described has been developed with current prosthetist methods as the primary design consideration. The PSF System software can include several advanced design options.

The PSF System Software can include a closed loop algorithm coefficient modeling module. Advanced robotic prostheses can involve control systems with high-bandwidth responsiveness, such as control systems that need to be carefully tuned, such as to match both machine and user limits. Data from the PSF System can be used to tune control parameters, such as "Proportional/Integral/Derivative" (PID) coefficients of active systems to match the resulting loads to the load-bearing capacity of the socket. In an example, exercises with the socket alone can be processed by the PSF System, such as to directly programs the response parameters of the active prosthetic attached to the socket.

The PSF System Software can include an anatomy modeling module. Modeling of the muscle and tendon anatomy of the limb can provide the prosthetist a clearer view of the role of soft tissue in the observed bone movement. In an example, to help guide fitment, an animated output showing the movement can be provided.

The PSF System Software can include an expert system module. Bone motion analysis coupled with standard exercises, 3D CAD socket modeling, and rapid manufacturing, can create a closed-loop socket creation tool.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A prosthetic socket fitment sensor system comprising:
a transceiver assembly, located within a transceiver cavity of an external frame fitted to a residual limb of a patient, configured to generate a signal and receive a reflected signal, the transceiver assembly including:
a transceiver device to generate a signal and receive a reflected signal,
a housing to locate the transceiver device with respect to the patient, the housing including a base with a first base surface and a second base surface generally parallel to the first base surface, and a cap with a cap surface generally parallel with the second base surface, wherein the cap is attached to the second base surface, and
a retainer to locate the transceiver device with respect to the housing; and
a processing module in electrical communication with the at least one transceiver assembly, wherein the processing module is configured to process the signal and the reflected signal,
wherein the housing includes a gap, located in the base and extending from the first base surface to the second base surface, which is configured to receive the transceiver assembly.

2. The prosthetic socket fitment sensor system of claim 1, wherein the base includes a base axis perpendicular to the first base surface, and the cap includes a cap axis perpendicular to the cap surface,
wherein the cap axis forms a non-zero angle with the base axis.

3. The prosthetic socket fitment sensor system of claim 1, wherein the transceiver assembly includes an ultrasonic transceiver device.

4. The prosthetic socket fitment sensor system of claim 1, comprising a scale located in proximity to the transceiver cavity and a witness mark located on the transceiver assembly, wherein the witness mark is capable of being located with respect to the scale to orient the transceiver assembly with respect to the external frame.

5. The prosthetic socket fitment sensor system of claim 1, wherein the transceiver assembly and the transceiver cavity assume a circular shape configured to allow the transceiver assembly to rotate with respect to the transceiver cavity when the transceiver assembly is located in the transceiver cavity.

6. The prosthetic socket fitment sensor system of claim 1, wherein the transceiver assembly and the transceiver cavity conform to an outer surface of the external frame.

7. The prosthetic socket fitment sensor system of claim 1, comprising a wire attached to the transceiver assembly, and wherein the processing module is configured to facilitate electrical communication between the transceiver assembly and the processing module.

8. The prosthetic socket fitment sensor system of claim 1, comprising a wireless transmission unit in communication with the processing module, wherein the wireless transmission unit is configured to facilitate wireless communication between the processing module and a personal computer.

9. The prosthetic socket fitment sensor system of claim 1, wherein the processing module includes an image capture unit configured to receive and process of a signal related to tissue thickness, and
a digital signal processing (DSP) module with a digital timer, wherein the DSP module is connected to the image capture unit and is configured to receive an indication of the processed signal related to tissue thickness and calculate an indication of tissue thickness.

10. The prosthetic socket fitment sensor system of claim 9, wherein the image capture unit includes an analog front-end (AFE) module configured to receive a signal from the transceiver device, and an analog signal conditioning (ASC) module configured to condition of the received signal from the AFE module.

11. The prosthetic socket fitment sensor system of claim 1, comprising a hole located in the cap surface which is configured to receive the transceiver assembly.

12. The prosthetic socket fitment sensor system of claim 1, wherein a distance between the base and the cap is selected to locate the transceiver assembly in contact with a dermis of the patient.

13. The prosthetic socket fitment sensor system of claim 1, wherein a distance between the base and the cap is selected to locate the transceiver assembly in contact with a liner of the external frame.

14. The prosthetic socket fitment sensor system of claim 1, wherein the retainer to locate the transceiver device with respect to the housing includes a fastener to connect the transceiver device to the housing.

15. The prosthetic socket fitment sensor system of claim 1, wherein the retainer to locate the transceiver device with respect to the housing includes an elastic loop to connect the transceiver device to the housing.

16. The prosthetic socket fitment sensor system of claim 1, comprising an active padding control system configured to modify padding forces applied by the external frame on the residual limb of the patient.

17. The prosthetic socket fitment sensor system of claim 16, wherein the active padding control system is oriented between the residual limb of the patient and the external frame, wherein the active padding control system includes a smart fabric capable of sensing a pressure to assist in socket padding design.

18. The prosthetic socket fitment sensor system of claim 1, wherein the processing module includes a counter configured to determine a distance from the transceiver assembly to a bone in the residual limb of the patient.

19. The prosthetic socket fitment sensor system of claim 1, including a second transceiver assembly in electrical communication with the processing module, wherein the second transceiver assembly is configured to form a bone image reconstruction system of the residual limb of the patient to provide information concerning the location, condition, and movement of the residual limb with respect to the external frame.

20. The prosthetic socket fitment sensor system of claim 1, comprising a smart exercise accessory, including a fixed weight and a load cell attached to the external frame, wherein the smart exercise accessory is configured to measure load reacted by the residual limb during use of the prosthetic socket fitment system.

* * * * *

UNITED STATES PATENT AND TRADEMARK OFFICE
CERTIFICATE OF CORRECTION

PATENT NO. : 10,226,363 B2
APPLICATION NO. : 15/185632
DATED : March 12, 2019
INVENTOR(S) : Sup, IV et al.

Page 1 of 1

It is certified that error appears in the above-identified patent and that said Letters Patent is hereby corrected as shown below:

On the Title Page

On page 2, in Column 1, under "Other Publications", Line 1, delete ""In?uence" and insert --"Influence-- therefor Signed and Sealed this
Seventh Day of April, 2020

Andrei Iancu
*Director of the United States Patent and Trademark Office*